United States Patent
Morris et al.

(10) Patent No.: US 12,371,333 B2
(45) Date of Patent: *Jul. 29, 2025

(54) PURIFICATION OF CLINOPTILOLITE

(71) Applicant: Revelation Health LLC, Allison Park, PA (US)

(72) Inventors: Shayne K. Morris, Ogden, UT (US); Firas S. Harb, Farmington, UT (US); Warren P. Phillips, Cranberry Township, PA (US); Daniel Pompa, Park City, UT (US)

(73) Assignee: Revelation Health LLC, Allison Park, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/135,286

(22) Filed: Apr. 17, 2023

(65) Prior Publication Data
US 2023/0322566 A1    Oct. 12, 2023

Related U.S. Application Data

(63) Continuation of application No. 17/067,330, filed on Oct. 9, 2020, now Pat. No. 11,629,060, which is a continuation-in-part of application No. PCT/US2019/027262, filed on Apr. 12, 2019.

(60) Provisional application No. 62/656,554, filed on Apr. 12, 2018.

(51) Int. Cl.
| | |
|---|---|
| C01B 39/02 | (2006.01) |
| A61K 9/127 | (2025.01) |
| A61K 33/06 | (2006.01) |
| A61P 39/06 | (2006.01) |

(52) U.S. Cl.
CPC ............ *C01B 39/026* (2013.01); *A61K 9/127* (2013.01); *A61K 33/06* (2013.01); *A61P 39/06* (2018.01)

(58) Field of Classification Search
None
See application file for complete search history.

(56) References Cited

U.S. PATENT DOCUMENTS

| | | |
|---|---|---|
| 6,288,045 B1 | 9/2001 | Kaufman |
| 7,083,572 B2 | 8/2006 | Unger et al. |
| 9,629,874 B2 | 4/2017 | Tsirikos-Karapanos |
| 10,202,284 B2 | 2/2019 | Usui et al. |
| 10,206,948 B2 | 2/2019 | Tsirikos-Karapanos |
| 10,828,324 B2 | 11/2020 | Tsirikos-Karapanos |
| 11,629,060 B2 | 4/2023 | Morris et al. |
| 2003/0105031 A1 | 6/2003 | Rosenbloom |
| 2005/0031708 A1 | 2/2005 | Portney |
| 2006/0115420 A1 | 6/2006 | Fellers |
| 2011/0064798 A1 | 3/2011 | Suvee et al. |
| 2016/0367595 A1 | 12/2016 | Tsirikos-Karapanos |

FOREIGN PATENT DOCUMENTS

WO    2016194956 A1    12/2016

OTHER PUBLICATIONS

Akkoca et al., "Hydrothermal and Thermal Treatment of Natural Clinoptilolite Zeolite from Bigadic, Turkey: An Experimental Study," Geochemistry International, vol. 51, No. 6, pp. 495-504 [Abstract Only] (2013), 1 page.
Ambrozova et al., "Synthesis and Modification of Clinoptilolite," Molecules, vol. 22(7), 1107, DOI:10.3390/molecules22071107, (2017), 13 pages.
Cook et al., "Zeolite a Hydrolysis and Degradation," Environ. Sci. Tech. 16; 6; pp. 344-350 (1982), 7 pages.
Delavarian et al., "Increasing performance in children with ADHD by trapping lead with a nano-zeolite," J Neuropsychiatry Clin Neurosci. 2013 Winter;25(1):E23, 1 page.
Eshraghi et al., "EDTA functionalized clinoptilolite nanoparticles as an effective adsorbent for Pb(II) removal," Environ. Sci. Pollut. Res. Int., vol. 25(14), [Abstract only], DOI:10.1007/s11356-018-1461-0 (May 2018), 2 pages.
Flowers et al., "Clinical evidence supporting the use of an activated clinoptilolite suspension as an agent to increase urinary excretion of toxic heavy metals," Nutrition and Dietary Supplements 2009:1, 11-18, (2009), 8 pages.
Hernandez-Beltran et al., "Effect of Acid Phosphate Media on the Stability of Clinoptilolite-Rich Tuff," J. Incl. Phenom. Macrocycl. Chem., vol. 61, pp. 93-100 [Abstract Only] (2008), 1 page.
Ikotun et al., "Strength and durability effect of modified zeolite additive on concrete properties," Construction and Building Materials, vol. 24, iss. 5, (May 2010), [Abstract only], 2 pages.
Jurkic et al., "Biological and Therapeutic Effects of Ortho-Silicic Acid and Some Ortho-Silicic Acid-Releasing Compounds: New Perspectives for Therapy," Nutrition and Metabolism, vol. 10, No. 2 (2013), 12 pages.
Lamprecht et al., "Effects of Zeolite supplementation on parameters of intestinal barrier integrity, inflammation, redox biology and performance in aerobically trained subjects," J. Int Soc Sports Nutr. 12:40, DOI:10.1186/s12970-015-0101-z (2015), 11 pages.
Morris, S., "Zeolite Evolution," Appendix A PCT Publication No. WO2019200278 (Pub. Date: Oct. 17, 2019), 15 pages.
Tomasevic-Canovic et al., "Purification of Natural Zeolite-Clinoptilolite for Medical Application-Extraction of Lead," J Serb Chem Soc, 70(11), pp. 1335-1345, (2005), 11 pages.
Uivarosi et al., "Flavanoid Compexes as Promising Anticancer Metallodrugs," in Flavonoids—From Biosynthesis to Human Health, Intech Open (Pub.), Chapter 14, pp. 305-333, DOI:10.5772/67879 (2017), 30 ages.

(Continued)

*Primary Examiner* — Celeste A Roney
(74) *Attorney, Agent, or Firm* — Barclay Damon LLP; Jerry Cohen

(57) ABSTRACT

Zeolites for extraction of heavy metals are given enhanced purification in a first method stage and further processed in a second method stage to form liquid and solid phases including swollen clinoptilolite fragments ranging from 200 to 2000 Daltons and formed as liposomes and usable to substantially reduce heavy metal ppm burdens for purposes of safe ingestion by mammals and reduction of heavy metal contaminants of gut, vascular and lymphatic systems of a mammalian host.

12 Claims, 6 Drawing Sheets

(56) References Cited

OTHER PUBLICATIONS

Wilkin et al., "Solubility and Stability of Zeolites in Aqueous Solution: I. Analcime, Na-, and K-Clinoptilolite," American Mineralogist, vol. 83, pp. 746-761 (1998), 16 pages.
International Search Report and Written Opinion issued in PCT/2019/027262 dated Jun. 17, 2019.
Office Communication in Reply to Third Party Submission in U.S. Appl. No. 17/067,330, dated Jul. 14, 2021, 2 pages.
Third Party Observation filed in Application No. PCT/US2019/027262, dated Mar. 6, 2020, 6 pages.
Third Party Submission Under 37 C.F.R. §1.290 as filed in U.S. Appl. No. 17/067,330 on Jul. 8, 2021, 14 pages.
Examination Report No. 1 in AU Application No. 2019252817, dated Mar. 21, 2023, 2 pages.
Examiner Requisition in CA Application No. 3,124,680 dated Mar. 29, 2023, 6 pages.
Examiner Requisition in Canadian Patent Application No. 3124680 dated Aug. 25, 2023, 4 pages.

|  | Arsenic | Cadmium | Lead | Mercury |
|---|---|---|---|---|
| Raw Material Clinoptilolite | 21.14 PPM | 0.49 PPM | 20.95 PPM | 0.038 PPM |
|  |  |  |  |  |
| Purified Clinoptilolite | 1.48 PPM | 0.26 PPM | 1.95 PPM | 0.001 PPM |
Figure 1, ICP-MS Data
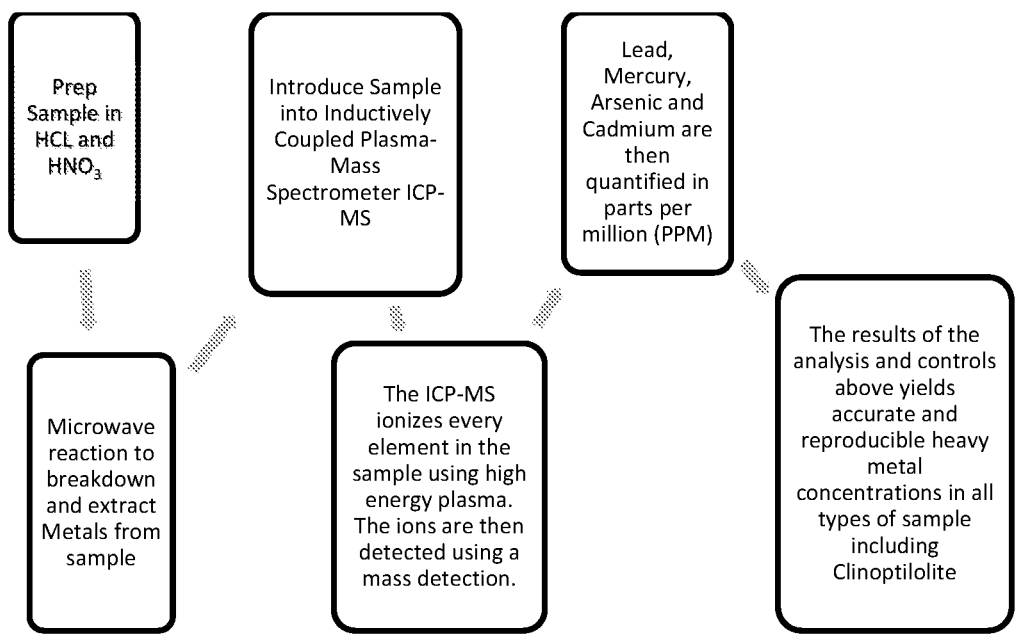
Figure 2 - Heavy Metal Testing Procedure

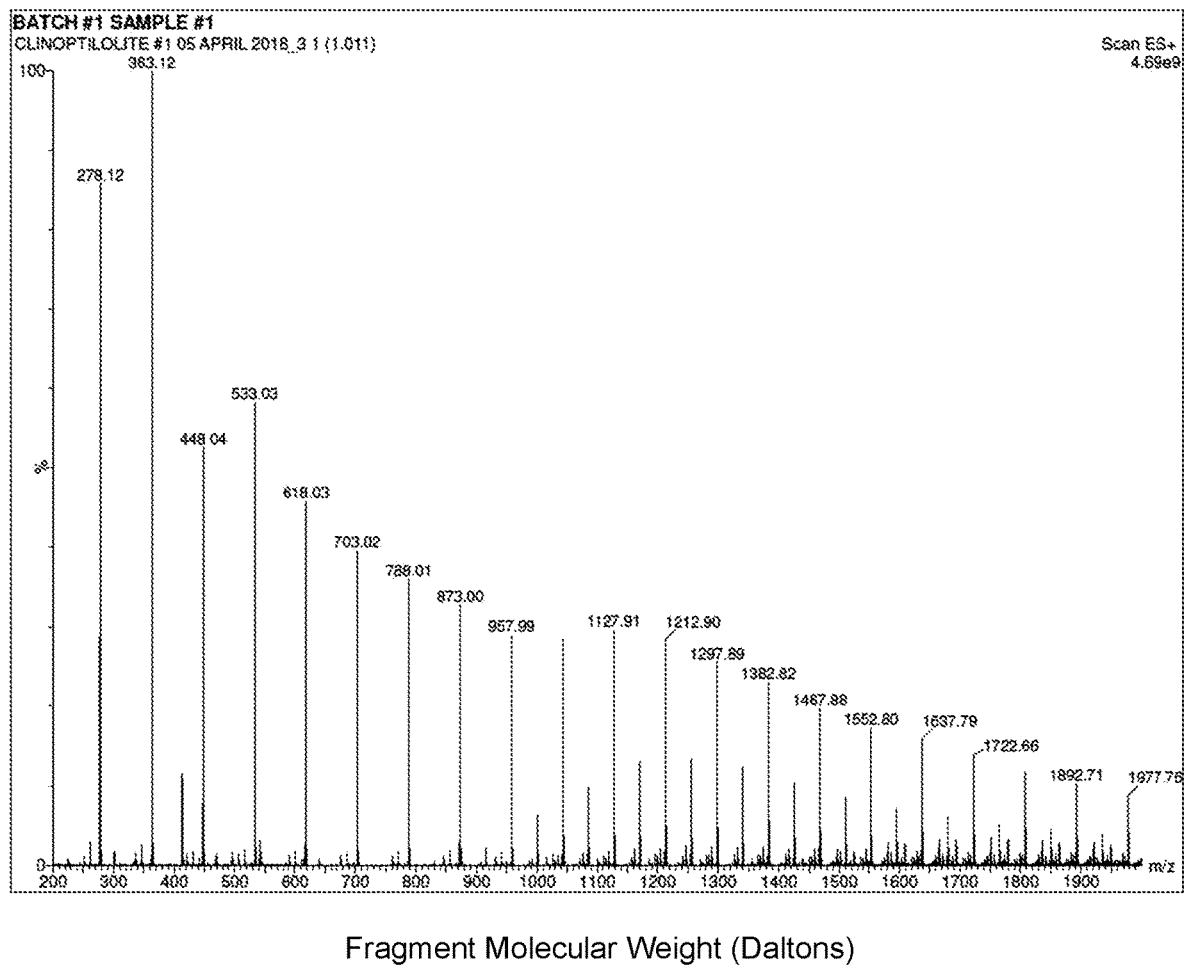
Figure 3A - Mass Spectral Data

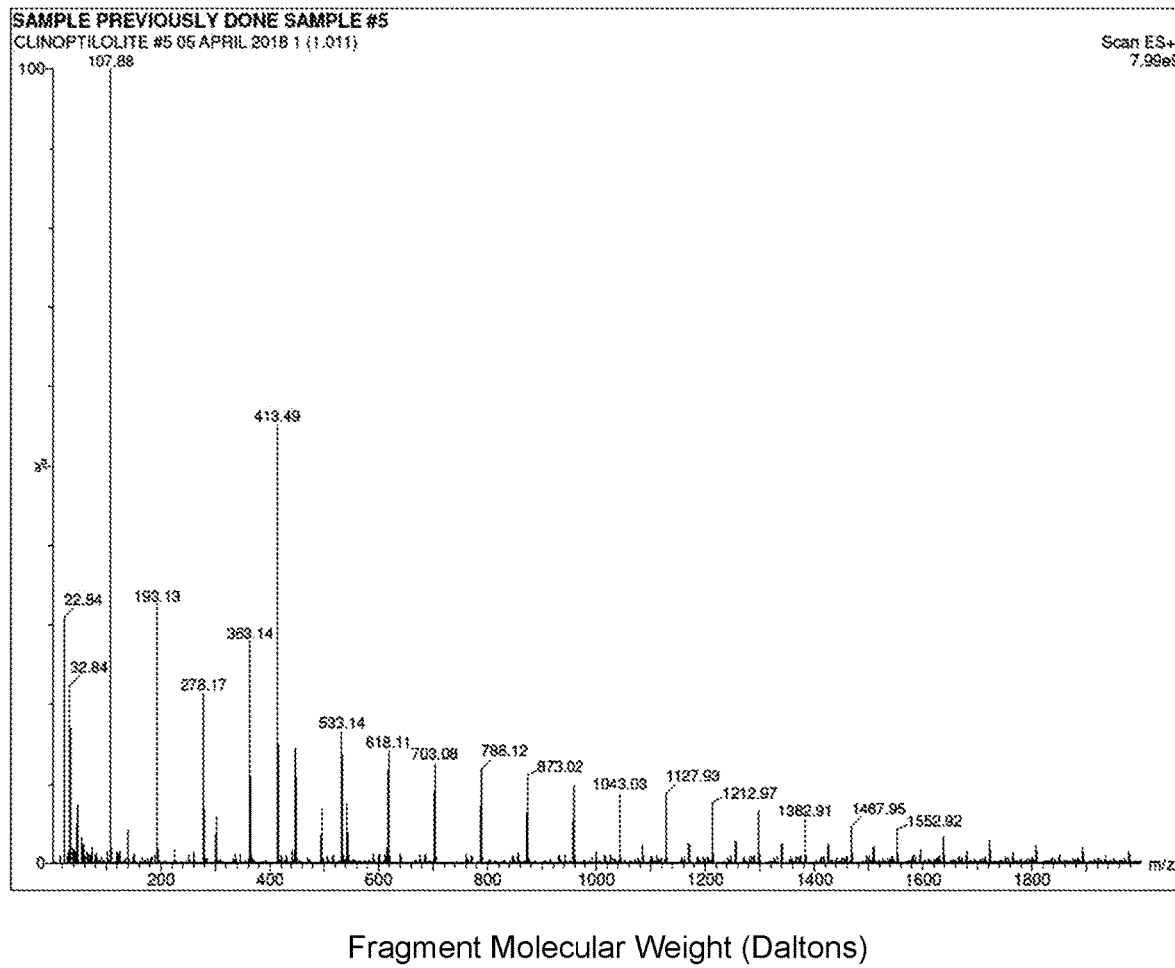
Figure 3B - Mass Spectral Data

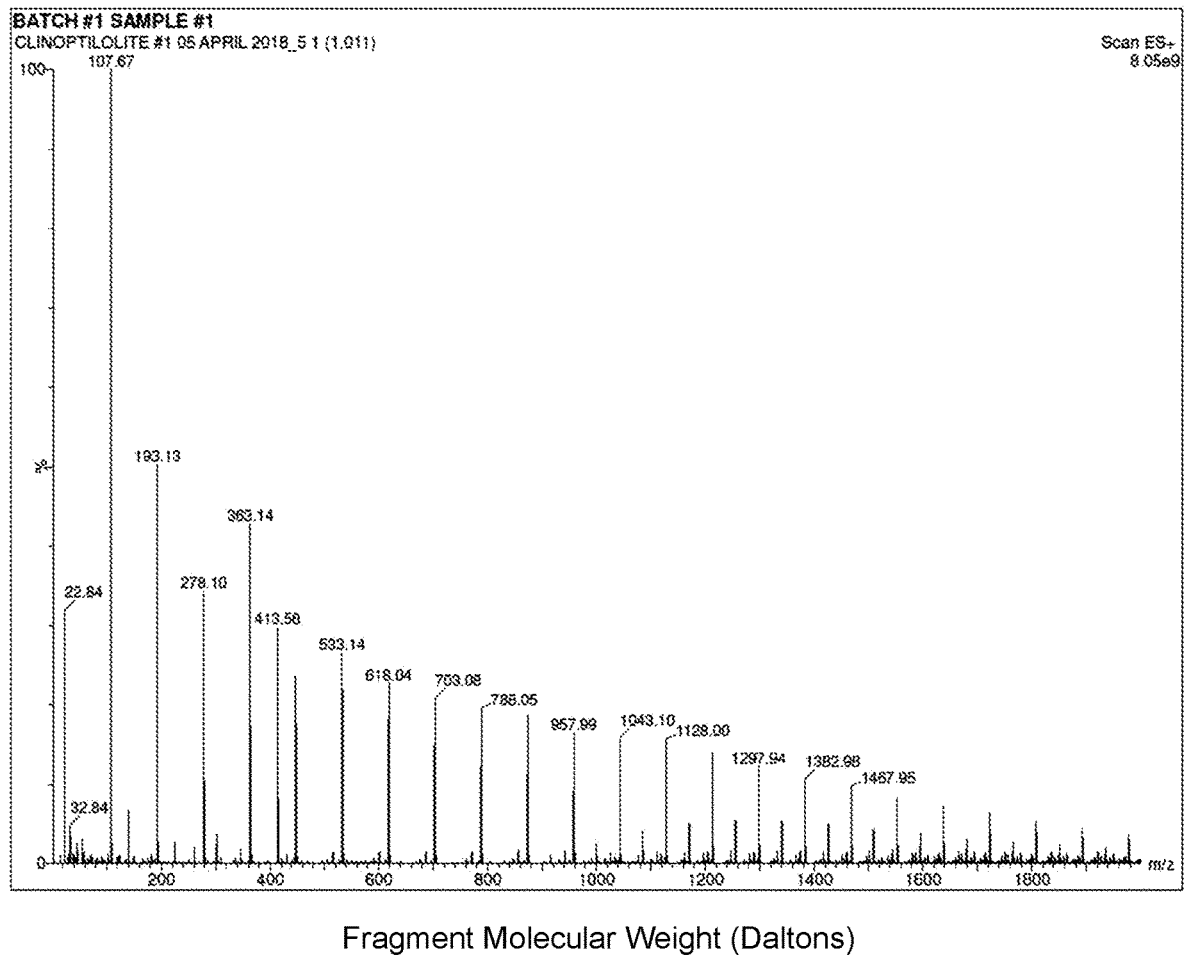
Figure 3C - Mass Spectral Data

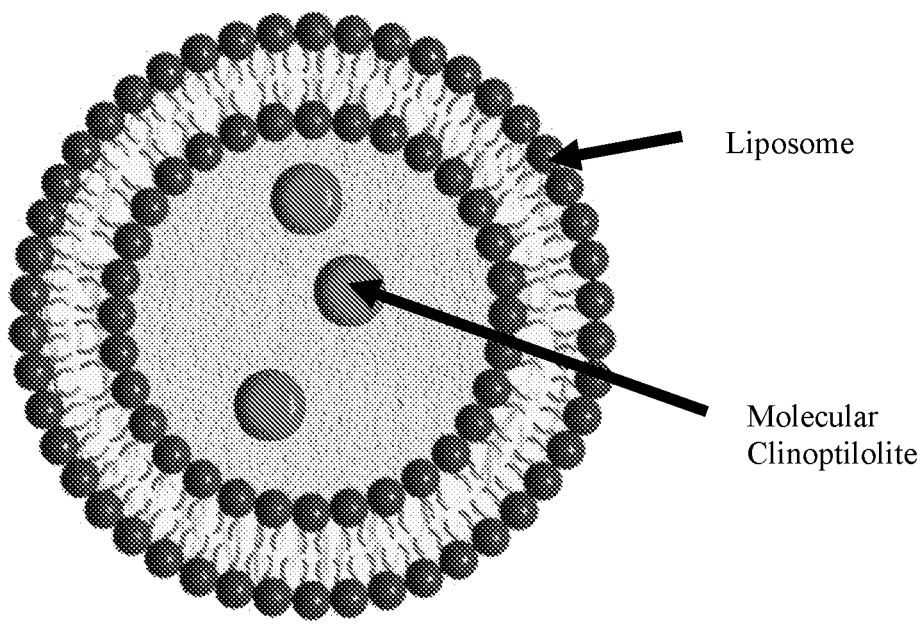
Figure 5A - Molecular Clinoptilolite Graphic
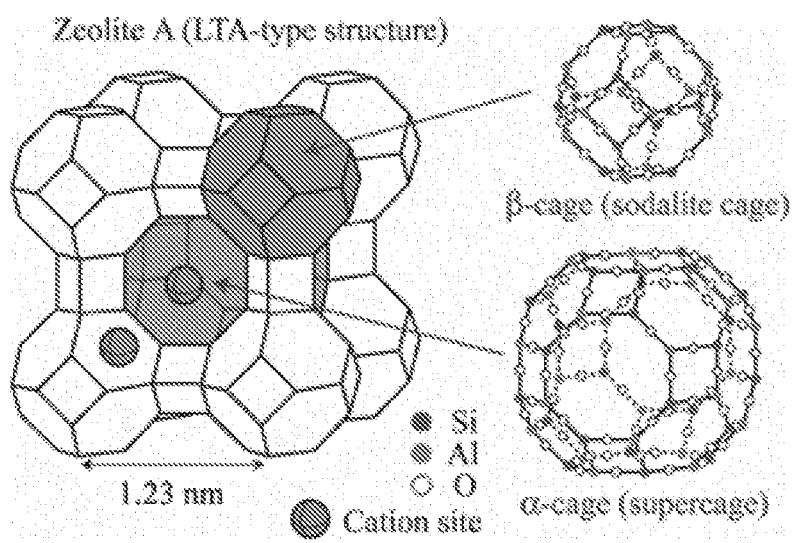
Figure 5B

PURIFICATION OF CLINOPTILOLITE

CROSS-REFERENCE TO RELATED APPLICATION

This application is a Continuation of U.S. patent application Ser. No. 17/067,330, filed on Oct. 9, 2020, which claims the benefit and priority to Continuation in Part of International Application PCT/US2019/027262, filed Apr. 12, 2019, which claims the benefit and priority under 35 U.S.C. § 119(e) to U.S. Provisional Application No. 62/656,554, filed on Apr. 12, 2018, entitled, "PURIFICATION OF CLINOPTILOLITE." The entire contents of these patent applications are hereby incorporated by reference herein.

FIELD OF THE INVENTION

The present invention relates to zeolites useful as cation exchangers for capturing GI tract (gut) and vascular and lymphatic systems toxic contaminants (toxins) and exhancing ability for such usage and other equivalent usage.

BACKGROUND

Clinoptilolite is exemplary of zeolites with exceptional cation exchange properties known for use in processes for extracting lead, arsenic, mercury, cadmium and like heavy metals in vitro or in vivo including removal of such metal contaminants from mammalian gut, blood and lymph. It has been used in dietary supplements along with beneficial vitamins and minerals. But, part of the reason for such mixing is for safety purposes to dilute the amount of zeolite dosage because of heavy metal loading of the ingested zeolite itself in its natural state and insufficient purification processing from natural mined state to use in formulations for removing heavy metal toxins. There is uncertainty in the art as to whether the toxins in clintoptilolite are released to mammalian host but the better view is that they are released; hence, the dilution practice. See references a-e below.

SUMMARY OF THE INVENTION

The present invention provides for creating purified clinoptilolite (or other target zeolites) to use alone as a dietary supplement or intermixed in a dietary supplement or converted to a molecular fragmented form, in all such instances being safe for ingestion without reliance on substantial dilution.

The purification process begins with a high quality clinoptilolite material per industry standards, but still too loaded with heavy metal cautions for human or animal usage in undiluted form. It is mixed with ethylene diamine tetraacetic acid (EDTA), preferably in a C:EDTA mass ratio between 3:1 and 5:1 and water added in a preferred volume ratio of water to mixture of 2:1 to 10:1, boiled with refluxing for sufficient time for substantially complete solution. Then one or more strong acids, preferably hydrochloric acid (HCL) or nitric acid ($HNO_3$), or mixture of them, are mixed into the solution in a volume of ratio mixtures to acid 10:1 to 1:1 and the combination is superheated, e.g. at 100° C. vs. 60° C. boiling temperature of the solution while maintaining refluxing control to avoid boiling over or dryness while producing a purified clinoptilolite solid in powder form. The boiled combination is cooled then filtered to remove powders above 0.2 microns of cross section dimension (diameter or equivalent diameter). The powder filtrate is tested for clear metal concentration, e.g. by inductively coupled plasma mass spectrometry (ICP-MS) and ready for usage as is for ingestion or for conversion as described next.

According to a second aspect of the invention the purified clinoptilolite solution described above is mixed with one or more strong acids (e.g. a solution for acid ratio of 10:1 to 1:1) reflux boiled or described above, typically at 100° c. for one hour, then cooled and neutralized by gradually adding a base (e.g. sodium hydroxide, NaOH) and stirring to create a suspension form of 4-7 pH and is tested. At this point there are solid and liquid phases including fragmented clinoptilolite fragments of a large range separated out by filtering to capture larger fragments while swollen molecular fragments remain dissolved in the liquid phase ranging from 200 to 2000 Daltons. These molecular fragments can be converted to liposome preparation methods including steps of dispersion and addition of liquid agents (e.g. phospholipids) optimally complemented with lecithin, glycerol, cholesterol and/or ethanol, and water. Also glutathione EDTA, flavonoids, alkaloids, terpenes, n-acetyl cysteine and zinc-lipoate to form molecular clinoptilolite liposome with or without additional active ingredients. The purified clinoptilolite solution from above may also be treated with NaOH instead of HCl (at a ratio of 1:1 to 1:8 NaOH to clinoptilolite). The solution is allowed to reflux under heat for a minimum of 30 minutes. Next, the solution is cooled to room temperature and neutralized with HCl to a pH of 4-7.

The resultant products of initially purified clinoptilolite as per the first aspect described above or as the molecular clinoptilolite liposomes exhibit substantial reduced burdens of heavy metals compared to the prior art clinoptilolite material and are usable for ingestion without heavy dilation and can more effectively reduce the heavy metals of mammalian gut, vascular or lymph systems and ultimately reaching tissue cells for extracating toxins and elimination in urine, thereby improving state of the art of cleansing heavy metals.

The present invention includes the above summarized processes toxins, including but not limited to, and resultant products made therefrom. It can be applied to zeolites other than clinoptilolite. Acids and liposome agents cited above can be substituted using the insights of the present invention.

Other object features and advantages of the present invention will be apparent to persons skilled in the art from the above and from the following description of embodiments of the process and product described in the following detailed description and accompanying drawings, in which:

BRIEF DESCRIPTION OF THE DRAWINGS

FIG. 1 is a table of the purification results;

FIG. 2 is a block diagram of heavy metal testing procedure;

FIGS. 3a, 3b, 3c are traces of mass spectral data for purified clinoptilolite;

FIGS. 5a, 5b are graphics of molecular clinoptilolite liposome.

DETAILED DESCRIPTION OF THE EMBODIMENTS

Figure 4:
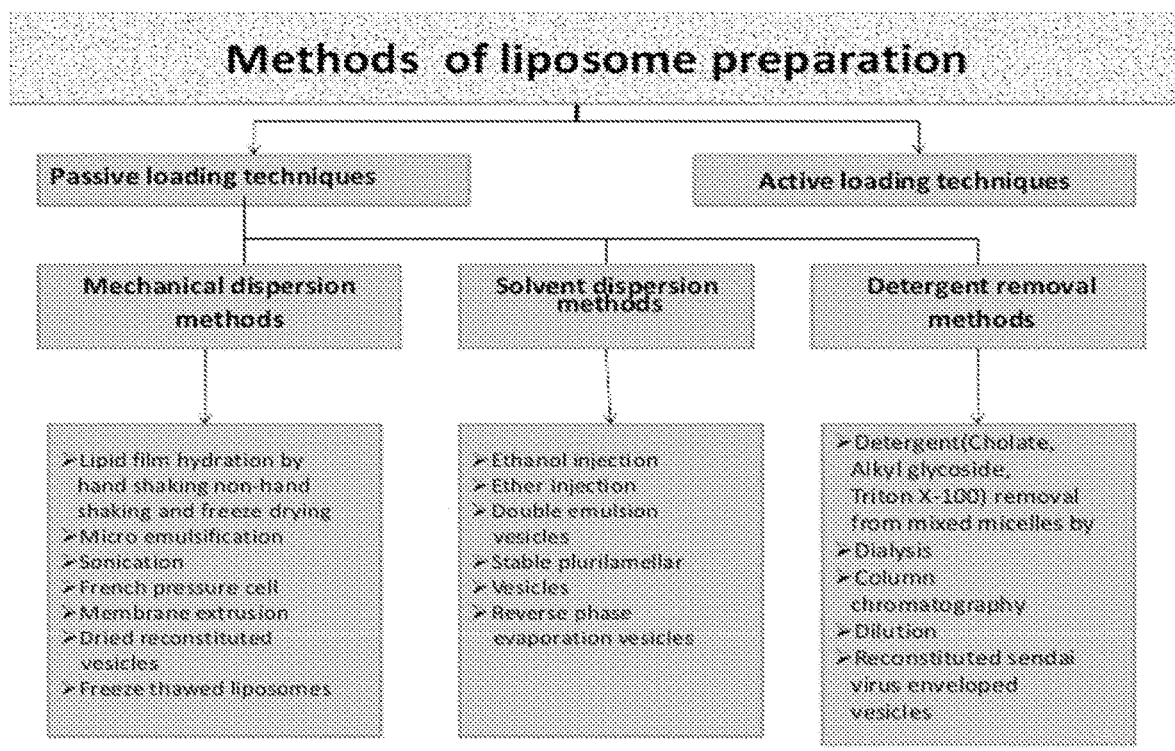
FIG. 4 is a table of liposome preparation alternative procedures.

Preparation of purified Clinoptilolite—Clinoptilolite is an exceptional cation exchanger and in its natural state inherently traps a number of cation heavy metals including: Lead (Pb), Arsenic (As), Mercury (Hg), Cadmium (Cd). Therefore, its use as a dietary supplement ingredient is restricted because the naturally occurring heavy metals can affect safety and regulatory limits. Most dietary supplements use reduced clinoptilolite concentrations in formulas. Thus, effectively diluting the benefit of clinoptilolite on order to dilute the heavy metals down to safe limits. The following process successfully reduces the heavy metal burden of the clinoptilolite material simultaneously improving its safety and effectiveness for use in formulas.

A. The purification process begins with the highest quality natural clinoptilolite.

B. The raw clinoptilolite is first dried in an oven at 200-220° C. for 4-8 hours to remove moisture.

C. Next, combine the raw clinoptilolite with Aqua Regia (3-parts HCL: 1-part HNO3). The ratio of Aqua Regia to clinoptilolite should be in the range of 6-9.

D. The mixture of clinoptilolite and acid is brought to a boil and refluxed for approximately 1.5 hours.

E. The mixture is then cooled and allowed to settle or centrifuged.

F. The top liquid layer (supernatant) is removed and discarded.

G. 1-2 Liters of 18 mega Ohm water is added to the clinoptilolite (ratio of water to clinoptilolite is in the order of 5-8) and brought to a boil along with mixing. The vessel is covered with a watch glass to allow it to reflux for 0.5-1 hours.

H. The mixture is then allowed to settle or centrifuged. The supernatant is then discarded.

I. Combine the clinoptilolite and Ethylene diamine tetraacetic acid (EDTA) at a ratio of between 2.5:1 to 5:1 by mass along with 2-10× liters of water. This step is designed to facilitate the removal of heavy metal from the clinoptilolite.

J. Stir the solution while heating to boil approximately 60 C for 1 hour. Vessel needs to be covered to allow for refluxing.

K. Allow the solution to cool and the clinoptilolite to settle (Centrifugation may be used in this step). Discard the supernatant.

L. The clinoptilolite powder is then dried at 200-220° C. for 4-8 hours.

M. Test the purified clinoptilolite for heavy metal concentration using ICP-MS (Inductively Coupled Plasma Mass Spectrometry). The ICP-MS testing procedure is described elsewhere. FIG. 1.

N. The dried and purified clinoptilolite is designed for use directly in a dietary supplement or to create molecular fragmented clinoptilolite in part 2;

Procedure for Fragmenting clinoptilolite into molecular pieces—Clinoptilolite fragments molecular weights produced during this process will range from 200 Daltons to over 2000 Daltons. The results of the fragmentation produce a broad range of clinoptilolite molecular sizes. The purpose these varying sizes allows for a number of unique uses and efficacies. The larger fragments remain insoluble but offer the greatest effective binding capacities for a wide variety of toxins including heavy metals, mycotoxins, xenotoxins and others. Physiologically they will remain in the gastrointestinal tract when ingested as a dietary supplement. The medium and small fragments are soluble making them more suitable for incorporation into liposomes. Liposomes provide an efficient delivery system into the blood stream or lymphatic system.

A. The molecular fragmentation process begins with the purified clinoptilolite.

B. Next add a combination of strong acids HCL and $HNO_3$ (volume of acid can be in a range of $1/10^{th}$ to equal amount by volume to the solution).

C. Raise the temperature to boiling 100° C. and continue to reflux in a semi-closed vessel for 1 hour and monitor to avoid boiling over and boiling to dryness.

D. Cool the solution and neutralized it. Gradually add sodium hydroxide (NaOH) while stirring until a pH that ranges from 4-7 is achieved.

E. Test the purified clinoptilolite for heavy metal concentration using ICP-MS (Inductively Coupled Plasma Mass Spectrometry).

F. The molecular (fragmented) clinoptilolite is now in two phases a solid which represents the large clinoptilolite and the liquid which represents the molecular fragments that range from 200 Daltons to greater than 2000 Daltons and they are soluble;

FIGS. 3A-C illustrate mass spectral data showing the results of the molecular clinoptilolite fragmentation procedure. Note the fragment sizes at the bottom of the graph. This data confirms the claim; more specifically, 3A is sample #1 done under combined LC/MS mode (200-2000 Daltons). 3B depicts previously prepared Clinoptilolite sample (sample #5) up to 2000 Daltons; and 3C Mass fragments up to 2000 Daltons;

Preparation of the Molecular Clinoptilolite Liposome.

A. The liposomes can be prepared in a number of ways. The methods are defined as Liposomal preparation is a well know process and can be completed using natural ingredients from the following list: Phosphatidyl choline, Phosphatidyl serine, Phosphatidyl ethanolamine, lecithin, glycerol, cholesterol, ethanol and water.

B. The active molecular clinoptilolite is suspended in distilled/RO water. Add glycerol to the aqueous solution.

C. Next, the phospholipids are dissolved in ethanol then they are introduced into the water solution under pressure while a high velocity mixer is mixing the entire solution;

TABLE #1

Typical Molecular Clinoptilolite Liposomal formulation
Molecular Clinoptilolite Liposome Preparation

| Ingredient | % | Concentration |
| --- | --- | --- |
| Water | 39-60% | |
| Ethanol | 13-25% | |
| Glycerol | 39-60% | |
| Phospholipid | 1-7% | 10-70 mg/mL |

D. Typical formulations used for human consumption can be assemble of based on the core formula described in Table 1. This is a liquid formula to be taken orally and dispensed via a dropper. The dropper allows for control over the dosage, so it can be used with people having different sensitivities, people of different toxin exposures and people with different constitutions. Adding additional ingredients would enhance the formulas toxin binding and toxin elimination ingredients. These can be directly added to the existing formula by adjusting the level of water. Important ingredients to include: Glutathione, EDTA, flavonoids, alkaloids, N-acetyl Cysteine, Fulvic Acid and Zinc-lipoate.

E. If any other ingredients from part D above are added, it is intended they be included into the aqueous step of the molecular clinoptilolite liposome process, only the water concentration will be adjusted to allow for it. The active ingredients (phosphatidylcholine and Clinoptilolite) will stay within the ranges set above.

TABLE #2

Example of Molecular clinoptilolite liposome with additional active ingredients.

| Ingredient | % | Concentration |
|---|---|---|
| Water | 39-60% | |
| Ethanol | 13-25% | |
| Glycerol | 39-60% | |
| Phosphoplipid | 1-7% | 10-70 mg/mL |
| Clinoptilolite | 0.1-0.5% | 1-5 mg/mL |
| Fulvic acid | 0.025-0.2% | 0.25-2 mg/mL |
| EDTA | 0.025-2.5% | 0.25-25 mg/mL |
| Activated Carbon | 0.025-2.5% | 0.25-25 mg/mL |
| Buckminsterfullerene | 0.025-1.5% | 0.25-15 mg/mL |

FIGS. 5A-B are graphics of molecular clinoptilolite liposome. More specifically, Benefits of the Molecular liposomal Clinoptilolite. Molecular liposomal clinoptilolite provides two unique and powerful benefits over other zeolites on the market. First, zeolite (clinoptilolite) has a long pedigree of use as a gastro intestinal toxin binding (ion exchange) agent. Although, clinoptilolites naturally contain over 20 parts per million heavy metals including (lead, arsenic, mercury, cadmium), prevailing assumptions assert that these heavy metals do not release from the clinoptilolite into the body when ingested. Lack of rigorous studies proving this assumption gives this issue real potential and zeolites may, in fact contribute to human heavy metal burdens when ingested. To get around this issue some formulations dilute dramatically the clinoptilolite thus also reducing its efficacy. This current product contains the first clinoptilolite to be cleaned of heavy metal contaminants, unlike all other products on the market, this zeolite now contributes less than 2 parts per million heavy metals. Therefore, this clinoptilolite can be used at higher more effective concentrations needed to bind heavy metals. Additionally, this clinoptilolite no longer exceeds regulatory and safety limits when used at effective levels. Preparing the liposomal molecules using the cleaned clinoptilolite provides a novel mechanism of delivering clinoptilolite to the tissues and the lymphatic system. This is the first formulation of its kind employing liposomes which contain cleaned molecular clipotilolite fragments. The benefit of this formulation is the liposome delivering the molecular fragments deeper into the tissues not just the gastrointestinal tract, also these particular fragments are larger (2000 Daltons) than other products which keeps the cage structure more intact. Below the β-cage is 1300 Dalton therefore this molecular process keeps the integrity of the cage. Because the cage is the central feature facilitating the binding (ion exchange) capacity of clinoptilolite.

[Additional information appears in Appendix A hereto entitled Zeolite Evolution]

Benefits of the Molecular Liposomal Clinoptilolite

Molecular liposomal clinoptilolite provides two unique and powerful benefits over other zeolites on the market. First, zeolite (clinoptilolite) has a long pedigree of use as a gastrointestinal toxin binding (ion exchange) agent. Although, clinoptilolites naturally contain over 20 parts per million heavy metals including (lead, arsenic, mercury, cadmium), prevailing assumptions assert that these heavy metals do not release from the clinoptilolite into the body when ingested. Lack of rigorous studies proving this assumption warrants precaution against zeolites in fact contributing to human heavy metal burdens when ingested. To get around this issue some formulations dilute dramatically the clinoptilolite thus also reducing its efficacy. The presently described product contains the first clinoptilolite to be cleaned of heavy metal contaminants, unlike all other products on the market, this present zeolite contributes less than 2 parts per million (ppm) heavy metals. Therefore, this clinoptilolite product can be used at higher more effective concentrations needed to bind heavy metals. Additionally, this clinoptilolite no longer exceeds regulatory and safety limits when used at effective levels.

Preparing the liposomal molecules using the cleaned clinoptilolite provides a novel mechanism of delivering clinoptilolite via vascular paths to bodily tissues and to the lymphatic system. This is the first formulation of its kind employing liposomes which contain cleaned molecular clipotilolite fragments. The benefit of this formulation is the liposome delivering the molecular fragments deeper into the tissues not just the gastrointestinal tract. Also, these particular fragments are larger (2000 Daltons) than other products which keeps the cage structure more intact. Below the β-cage is 1300 Dalton therefore this molecular process keeps the integrity of the cage. Because the cage is the central feature facilitating the binding (ion exchange) capacity of clinoptilolite.

A practical formal for use of this mechanism includes a dietary supplement of clintoptilolite with a serving size of 0.5-1.0 milli-liter with 2.5 mg. clinoptilolite, 25 mg. phosphatidylcholine and 0.5 mg. of toluates and also water, glycerin, ethanol and EDTA, taken orally 2 or 3 times daily.

Various uses and further exposition of the present invention are shown in the slide set of Appendix A hereto, the content of which is incorporated herein.

(3.) REFERENCES a. Environ. Sci. Tech. 16; 6; 1982. Cook. T. etal. Zeolite a Hydrolysis and Degradation.
b. Nutrition and Dietary Supplements 2009:1 11-18 11. Flowers. J. etal; Clinical evidence supporting the use of an activated clinoptilolite suspension as an agent to increase urinary excretion of toxic heavy metals.
c. J. Int Soc Sporots Nutr. 2015; 12: 40. Schippihnger G. etal; Effects of Zeolite supplementation on parameters of intestinal barrier integrity, inflammation, redox biology and performance in aerobically trained subjects.
d. *Environ Sci Pollut Res Int.* 2018 Mar. 8, EDTA functionalized clinoptilolite nanoparticles as an effective adsorbent for Pb(II) removal. Eshraghi F[1,2], Nezamzadeh-Ejhieh A[3,4,5]
e. J Neuropsychiatry Clin Neurosci. 2013 Winter; 25(1): E23; Increasing performance in children with ADHD by trapping lead with a nano-zeolite. Delavarian M, Hassanvand A, Gharibzadeh S.

What is claimed:

1. A method of purification and fragmentation of clinoptilolite comprising the steps of:
   a) refluxing a mixture of dry clinoptilolite and Aqua Regia;
   b) allowing the mixture to cool and the clinoptilolite to settle prior to removing and discarding the supernatant, thereby producing isolated clinoptilolite;
   c) mixing the isolated clinoptilolite with 18 Mega Ohm water;
   d) allowing the mixture to settle prior to removing and discarding the supernatant, thereby purifying the clinoptilolite; and e) performing a reaction with the purified clinoptilolite, HCl, HNO$_3$ and NaOH to create a molecular liposomal form of the clinoptilolite with molecular fragments.

2. A molecular fragmented clinoptilolite product as made by the process of claim 1.

3. A method of cleansing metal toxins from a mammalian host by administering the product of claim 2.

4. The method of claim 1, wherein steps c) and d) are repeated for a total of three times.

5. The method of claim 1, comprising, before step a), drying raw clinoptilolite to remove moisture, thereby producing dry clinoptilolite.

6. The method of claim 5, wherein the raw clinoptilolite is dried in an oven at 220-200° C.

7. The method of claim 6, wherein the raw clinoptilolite is dried for 4-8 hours.

8. The method of claim 1, wherein the ratio of Aqua Regia to dry clinoptilolite is in the range of 6-9.

9. The method of claim 1, wherein the mixture of dry clinoptilolite and Aqua Regia is refluxed for 1.5 hours.

10. The method of claim 1, wherein the ratio of 18 Mega Ohm water to isolated clinoptilolite is in the range of 5-8.

11. The method of claim 1, wherein before step d), the mixture of isolated clinoptilolite and 18 Mega Ohm water is refluxed for 0.5-1 hour.

12. The method of claim 1, wherein the molecular liposomal form of the clinoptilolite contributes less than 2 parts per million heavy metals.

* * * * *